(12) United States Patent
Hitchman et al.

(10) Patent No.: US 6,365,022 B1
(45) Date of Patent: Apr. 2, 2002

(54) GAS SENSOR

(75) Inventors: Michael L. Hitchman; Migeun Park, both of Glasgow (GB)

(73) Assignee: Alphasense Limited, Great Dunmow Essex (GB)

( * ) Notice: Subject to any disclaimer, the term of this patent is extended or adjusted under 35 U.S.C. 154(b) by 0 days.

(21) Appl. No.: 09/527,965

(22) Filed: Mar. 17, 2000

(30) Foreign Application Priority Data

Mar. 19, 1999 (GB) .............................................. 9906424

(51) Int. Cl.⁷ .............................................. G01N 27/407
(52) U.S. Cl. ...................... 204/426; 204/427; 205/784
(58) Field of Search ................... 204/421–429

(56) References Cited

U.S. PATENT DOCUMENTS 3,764,269 A * 10/1973 Oldham et al.
3,821,090 A * 6/1974 Topol et al.
4,388,155 A * 6/1983 Chamberland et al.
5,128,020 A * 7/1992 Yamauchi et al.
5,322,611 A * 6/1994 Zaromb
6,241,873 B1 * 6/2001 Namba et al.

FOREIGN PATENT DOCUMENTS

| JP | 62-184450 | 8/1986 |
| JP | 62-271447 | 12/1986 |
| JP | 62-142266 | 6/1987 |
| JP | 62-207952 | 9/1987 |

* cited by examiner

Primary Examiner—T. Tung
(74) Attorney, Agent, or Firm—Jackson Walker LLP

(57) ABSTRACT

A gas sensor comprising an electrolytic cell having detecting and reference electrodes connected by a solid electrolyte. In a first embodiment, both electrodes comprise $Ag_2CO_3$ and $Ag_4RbI_5$, and the electrolyte is $Ag_4RbI_5$, the reference electrode being in contact with a reference gas. In a second embodiment, the reference electrode is a silver electrode and no reference gas is needed. The sensor is operable at room temperature to measure $CO_2$ concentrations, and is relatively unaffected by water vapor.

17 Claims, 5 Drawing Sheets

THE STRUCTURE OF AN OPEN GAS TYPE
CARBON DIOXIDE DETECTION SENSOR A

THE STRUCTURE OF AN OPEN GAS TYPE CARBON DIOXIDE DETECTION SENSOR A

THE STRUCTURE OF A GAS TIGHT TYPE CARBON DIOXIDE DETECTION SENSOR B

THE APPARATUS AA OF THE OPEN GAS TYPE CARBON DIOXIDE DETECTION SENSOR A

THE APPARATUS BA OF THE GAS TIGHT TYPE CARBON DIOXIDE DETECTION SENSOR B

THE STRUCTURE OF A DEVICE FOR MEASURING THE CELL POTENTIAL OF THE CARBON DIOXIDE DETECTION SENSOR RELATIVE TO GASEOUS CARBON DIOXIDE

CELL POTENTIAL AT 25°C AS A FUNCTION OF THE LOG OF THE CARBON DIOXIDE CONCENTRATION IN ANHYDROUS AIR FOR OPEN GAS TYPE CARBON DIOXIDE DETECTION SENSOR A

CELL POTENTIAL AT 25°C AS A FUNCTION OF THE LOG OF THE CARBON DIOXIDE CONCENTRATION IN ANHYDROUS AIR FOR GAS TIGHT TYPE CARBON DIOXIDE DETECTION SENSOR B

CELL POTENTIAL AT 25°C AS A FUNCTION OF THE LOG OF THE CARBON DIOXIDE CONCENTRATION IN AIR WITH 60% RELATIVE HUMIDITY FOR A GAS TIGHT TYPE CARBON DIOXIDE DETECTION SENSOR B

CELL POTENTIAL AT 25°C FOR 8000 PPM OF CARBON DIOXIDE AS A FUNCTION OF THE RELATIVE HUMIDITY FOR A GAS TIGHT TYPE CARBON DIOXIDE DETECTION SENSOR B

CELL POTENTIAL AS A FUNCTION OF ABSOLUTE TEMPERATURE FOR 2800 PPM OF CARBON DIOXIDE IN ANHYDROUS AIR FOR A GAS TIGHT TYPE CARBON DIOXIDE DETECTION SENSOR B

FIG. 11

THE TIME RESPONSE TO A STEP CHANGE IN GASEOUS CARBON DIOXIDE IN ANHYDROUS AIR FOR A GAS TIGHT TYPE CARBON DIOXIDE DETECTION SENSOR B

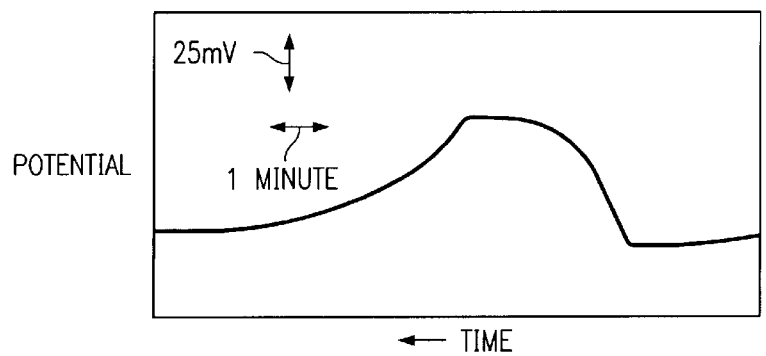

FIG. 12

THE TIME RESPONSE TO A STEP CHANGE IN GASEOUS CARBON DIOXIDE IN 60% HUMID AIR FOR A GAS TIGHT TYPE CARBON DIOXIDE DETECTION SENSOR B

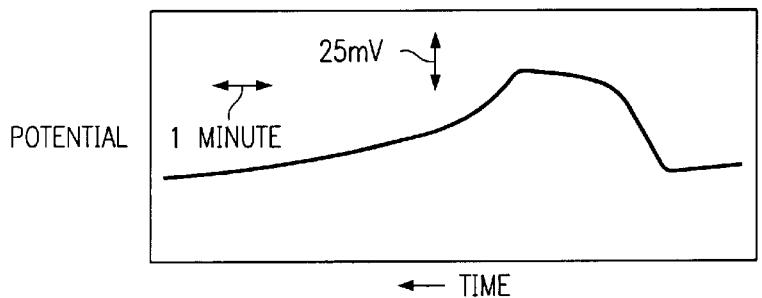

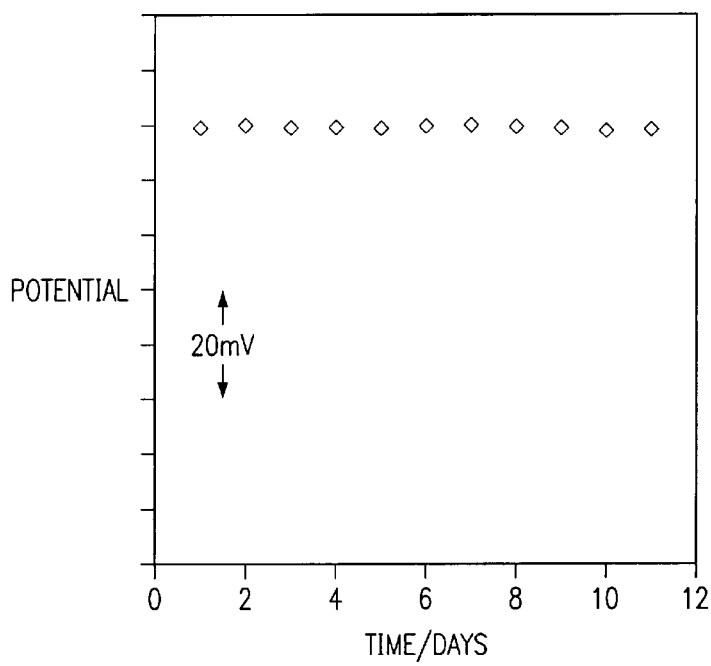

FIG. 13

PLOT OF CELL POTENTIAL FOR 960 PPM OF CARBON DIOXIDE IN ANHYDROUS AIR AT 25°C FOR A GAS TIGHT TYPE CARBON DIOXIDE DETECTION SENSOR B

GAS SENSOR

The present invention relates to a solid electrolyte type gas sensor and, more particularly, to a sensor operable at or about ambient temperature.

Solid electrolyte sensors at present comprise a detection electrode and a reference electrode disposed on opposite sides of a solid electrolyte acting as an ionic conductor. Generally, in detecting gaseous components present in an atmosphere using a solid electrolyte sensor, an ionic conductor is used in which specific ions are mobile and sometimes in combination with this specific ion conductor, which is used as the solid electrolyte, another compound containing the specific ions is used as a detection material and is covered by an electrocatalytic material, such as platinum.

JP-A-62-142266 describes an $NO_x$ sensor comprising a gold electrode on an insulating substrate, a solid $RbAg_4I_5$ electrolyte, and a gold detection electrode with $AgNO_3$ deposited on it to act as an electrocatalyst. Such a sensor requires a reference gas in contact with the reference electrode to provide a stable output potential. The $NO_x$ sensors of JP-A-61-271447 and JP-A-61-184450 have similar requirements. JP-A-62-207952 describes a halogen gas sensor having a reference electrode comprising a metal halide, metal, and a metal ion-conductive solid electrolyte. The cell electrolyte is a halide-containing metal ion-conductive solid electrolyte, and the detection electrode is said to be a metal halide-metal ion-conductive solid electrolyte mixture. The detection electrode does not have an electrocatalyst layer; the operating temperature of this sensor is 150° C.

A previously proposed gaseous carbon dioxide sensor uses, for example, a sodium ionic conductor such as β-alumina (general formula: $Na_2O \cdot nAl_2O_3$, n=5–11) or NASICON (general formula: $Na_{1-x}Zr_2P_{3-x}Si_xO_{12}$). In this case, a platinum gauze covered with sodium carbonate or the like is used as a detection electrode.

A typical reference electrode comprises gold or platinum alone or these metals covered with sodium carbonate or the like, maintained in contact with reference atmosphere of standard air or gaseous carbon dioxide. Accordingly, gaseous carbon dioxide at the concentration to be measured is in contact with the detection electrode but not with the gas reference electrode on the opposite side.

The sensor is heated during operation usually to a constant temperature between 400° C. and 600° C., a flux of sodium ions being caused to move to the detection electrode corresponding to the partial pressure of the gaseous carbon dioxide in a gas to be detected which is in contact with the detection electrode. This gives rise to a sodium ion gradient between the electrodes and the concentration of the gaseous carbon dioxide can be deduced by measuring the potential difference associated with this gradient.

However, in the case of the existing gaseous carbon dioxide sensors using sodium carbonate as the detection material for the detection electrode and using NASICON for the ionic conductor as described above, the potential difference is highly sensitive to the moisture content of the gas to be detected.

In order to overcome this effect, a gaseous carbon dioxide detection sensor comprising a detection electrode and a reference electrode on both sides of an ionic conductor with a mixture of one mole of an alkali metal carbonate and more than one mole of an alkaline earth metal carbonate such as $BaCO_3$ has been suggested as the material for the detection electrode. For such a sensor the variation of potential difference with carbon dioxide content is less affected by moisture in the gas to be measured.

A shortcoming of even this improved sensor is the operating temperature, which requires a heater. This elevated operating temperature is also a potential cause of accelerated breakdown of the sensor structure and problems associated with oxidation of electrocatalysts and contacts. Furthermore, in many cases, a reference gas is required which complicates the cell design and affects portability.

The present invention overcomes the foregoing problems in the prior art and provides a gas, especially carbon dioxide, detection sensor capable of measuring the concentration of a gas without the need for high temperature operation. Conveniently, the sensor may be operated at a controlled ambient or moderately elevated temperature, for example up to 70° C., to avoid any possible error resulting from ambient temperature variation. In one embodiment the use of a reference gas is avoided.

The present invention provides in a first aspect a gas sensor containing an electrolytic cell comprising a reference electrode, a detection electrode, and a solid electrolyte, the detection electrode comprising an electrocatalyst and a silver salt the anion of which corresponds to the gas to be detected, the solid electrolyte being capable of transmitting silver ions, and the reference electrode comprising metallic silver in contact with the electrolyte, the free face of the silver being sealed. A cell of this type is referred to below as one of the closed gas type.

As the gas to be detected, there may be mentioned, for example, sulphur trioxide, sulphur dioxide, nitrogen oxides ($No_x$, or specific nitrogen oxides), hydrogen sulphide and halogen, especially chlorine, or pseudohalogen, for example, cyanogen. The corresponding anion in the detection electrode is sulphate, sulphite, an oxyacid of nitrogen, and halide, especially chloride, or pseudohalide, for example, cyanide. More especially, and preferably, the gas to be detected is carbon dioxide and the corresponding anion is a carbonate.

The reference electrode is advantageously a metallic silver sheet in contact with the silver ion conductor.

In a second aspect the present invention provides a carbon dioxide sensor containing an electrolytic cell comprising a reference electrode, a detection electrode, and a solid electrolyte, the detection electrode comprising an electrocatalyst and silver carbonate, and the solid electrolyte being capable of transmitting silver ions.

In a first embodiment of the second aspect of the invention, a reference electrode having the same characteristics as set out below for the detection electrode is advantageously used, and preferably the reference electrode is of the same materials, and in the same proportion, as is the detection electrode.

Advantageously, in the first embodiment of the second aspect an atmosphere of a known constitution (a reference atmosphere) is maintained at the free face of the reference electrode. The reference atmosphere is advantageously air at atmospheric pressure with a known and constant $CO_2$ partial pressure. A cell of this type is referred to below as one of the open gas type.

In a second embodiment of the second aspect, the reference electrode is sealed. In this second embodiment the reference electrode is advantageously metallic silver in contact with the silver ion conductor. A cell of this type is referred to below as one of the closed gas type.

In each aspect, the detection electrode, in addition to a silver salt of an acid corresponding to the gas to be detected (carbonate in the second aspect), advantageously also contains a component that enhances the conductivity of the electrode. This component is advantageously an ionic conductor, and one through which silver ions may pass, preferably at room temperature, and may comprise a silver salt or double salt, for example, silver iodide or, advantageously, a silver rubidium iodide, especially $Ag_4RbI_5$, or a silver mercury iodide. Advantageously, the proportion of conductivity enhancer is adequate to provide a sufficiently high ionic conductivity.

The detection electrode advantageously also comprises a binder, e.g., polytetrafluorethylene (PTFE), in a proportion sufficient to render the conductive materials coherent but without adversely affecting conduction to a deleterious extent.

As solid electrolyte, there is advantageously used an ionic conductor, for example and preferably one mentioned above as the conductivity enhancer in the detection electrode, and more preferably the same ionic conductor as is used in that electrode. The electrolyte advantageously also comprises a binder, conveniently the same as that used in the electrode.

In each aspect, the detection electrode comprises an electrocatalyst advantageously in the form of a layer permeable to the gas to be detected, for example, platinum. A similar catalyst is advantageously provided on the free face of the reference electrode in the first embodiment of the second aspect.

Advantageously, platinum leads are provided to the detection electrode and in the first embodiment of the second aspect to the reference electrode. Although the reference electrode in the first aspect and the second embodiment of the second aspect may be provided with a platinum lead, other conductive leads may be used.

The apparatus in which the cell is placed is described in greater detail below. The cell itself is conveniently in the form of a disk.

The present invention more especially concerns a solid electrolyte type carbon dioxide sensor based on silver compounds which have been shown to have a good response to carbon dioxide concentration at room temperature. In particular, the present invention advantageously includes the presence as electrolyte, conductivity enhancer, or both, of silver rubidium iodide which is an excellent ionic conductive material at room temperature (the ionic specific conductivity of silver rubidium iodide is as high as $0.24(\text{ohm cm})^{-1}$ at 25° C.) which allows it to be used in the detection of carbon dioxide concentrations at ambient or near ambient temperatures.

Two different embodiments of carbon dioxide sensor based on silver compounds will be described in more detail, and will be referred to hereinafter for convenience as the open gas type and the gas tight type.

The open gas type of carbon dioxide gas sensor comprises the following electrochemical cell:

$$CO_2, O_2, N_2|Pt|Ag_2CO_3+Ag_4RbI_5|Ag_4RbI_5|Ag_2CO_3+Ag_4RbI_5|Pt|Air$$

where the right hand electrode is the reference electrode and the left hand electrode is the detecting electrode.

The detecting electrode equilibrium is $$Ag_2CO_3{'} \leftrightharpoons 2Ag^+ + CO_2{'} + 1/2O_2{'} + 2e^-$$

and the reference electrode equilibrium is $$2Ag^+ + CO_2{''} + 1/2O_2{''} + 2e^- \leftrightharpoons Ag_2CO_3{''}$$

The overall equilibrium is thus

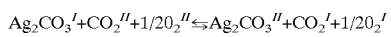

and the cell potential(E) is given by $$E=(\Delta G°_{Ag2CO3II}+\Delta G°_{CO2I}+½\Delta G°_{O2I}-\Delta G°_{Ag2CO3I}-\Delta G°_{CO2II}-½\Delta G°_{O2II})/2F-(RT/2F)\times \ln P_{CO_2}$$

where $\Delta G°_i$ is the standard free energy of formation for species i, F the Faraday constant, R the gas constant, T the absolute temperature, and $P_{CO_2}$ the partial pressure of $CO_2$. It is assumed in the equation that the activity of $Ag_2CO_3$ is unity. The silver rubidium iodide does not participate in electrode or cell reactions. It is present only as an ionic conductor.

Secondly, the gas tight type of carbon dioxide gas sensor comprises the following electrochemical cell:

$$CO_2, O_2, N_2|Pt|Ag_2CO_3+Ag_4RbI_5|Ag_4RbI_5|Ag$$

The detecting electrode equilibrium is

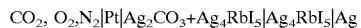

and the reference electrode equilibrium is

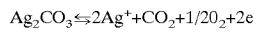

The overall equilibrium is thus

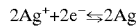

and the cell potential (E) is given by $$E=(2\Delta G°_{Ag}+\Delta G°_{CO2}+1/2\Delta G°_{O2}-\Delta G°_{Ag2CO3})/2F-(RT/2F)\times \ln P_{CO_2}$$

where the symbols have the meanings give above. It is assumed in the equation that the activities of $Ag_2CO_3$ and Ag are unity.

In this gas tight type carbon dioxide gas sensor the detecting electrode is open to the test gas but the silver reference electrode is sealed, and therefore in this gas tight type sensor there is no need to supply a separate reference gas.

BRIEF DESCRIPTION OF THE DRAWINGS

Two sensors constructed in accordance with the invention will now be described in greater detail by way of example with reference to accompanying drawings, in which:

FIG. 11 is a characteristic time response to step changes in carbon dioxide concentration between 4600 ppm and 8800 ppm in anhydrous air for a gas tight carbon dioxide detection sensor B.

FIG. 12 is a characteristic time response to step changes in carbon dioxide concentration between 4600 ppm and 8800 ppm in air with 60% relative humidity for a gas tight carbon dioxide detection sensor B.

FIG. 13 is a characteristic plot showing the temporal stability of the cell potential for 960 ppm of carbon dioxide in anhydrous air at 25° C. for a gas tight carbon dioxide detection sensor B.

FIG. 1 shows a structure of an open gas type carbon dioxide detection sensor A according to the present invention. In the figure are shown a thin platinum black layer 1 as electrocatalyst for a detection electrode 2 and another thin platinum black layer 5 as electrocatalyst for a reference electrode 4. The detection electrode electrolyte 2 and the reference electrode electrolyte 4 comprise silver carbonate and silver rubidium iodide and polytetrafluoroethylene (PTFE) powder as a binder. Between the electrodes is provided an ionic conductor 3 comprising silver rubidium iodide and PTFE powder.

FIG. 2 shows a structure of a gas tight type carbon dioxide detection sensor B according to the present invention. In the figure is shown a thin platinum black layer 6 as electrocatalyst for a detection electrode electrolyte 7. The detection electrode electrolyte 7 comprises silver carbonate and silver rubidium iodide and PTFE powder as a binder. There are also shown the ionic conductor 8 comprising silver rubidium iodide and PTFE powder and a silver metal layer 9 forming the reference electrode electrocatalyst.

Figure 1:
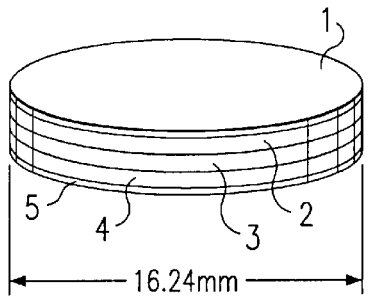
FIG. 1 is a view illustrating the structure of an open gas type carbon dioxide detection sensor A according to the present invention.
Figure 2:
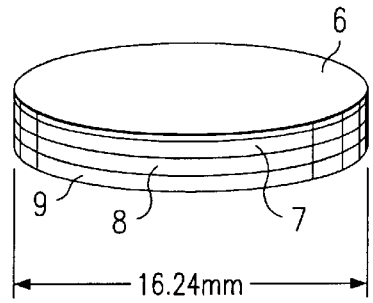
FIG. 2 is a view illustrating the structure of a gas tight type carbon dioxide detection sensor B according to the present invention.

The sensors A and B in FIGS. 1 and 2 are shown as having been assembled from discrete layers, but the sensors may also be made by any thin film deposition method, many of which are known to those skilled in the art. Examples include screen printing, sputtering, and vapour phase deposition. Further, since the electrodes comprise an electrolyte, the solid electrolyte of the cell may be provided by the electrode electrolyte, resulting in an integral cell construction.

Figure 3:
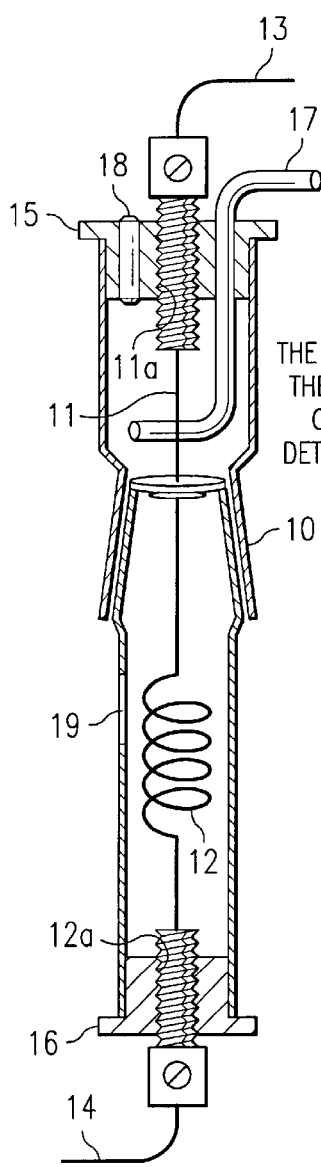
FIG. 3 is a view illustrating apparatus AA comprising the open gas type carbon dioxide detection sensor A according to the present invention.

FIG. 3 shows an apparatus AA containing an open gas type carbon dioxide detection sensor A according to the present invention. The carbon dioxide detection sensor A is set in a quartz cone 10 and platinum wire detection lead 11 and reference lead 12 are connected to opposite faces of the sensor A for detecting the potential. As shown in the figure, both ends of quartz cone 10 are closed with PTFE lids 15, 16 which allow platinum wires 11 and 12 to be connected to copper leads 13 and 14, respectively. The screw threads 11a and 12a allow the pressure of the contact wires to be varied. Set in the PTFE lid 15 on the detection side are a test gas inlet tube 17 and an outlet tube 18. An aperture 19 on the reference side of the quartz cone 10 allows a flow of reference air.

Figure 4:
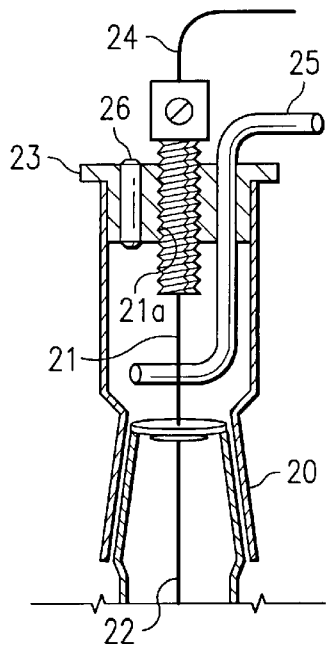
FIG. 4 is a view illustrating apparatus BA comprising the gas tight type carbon dioxide detection sensor B according to the present invention.

FIG. 4 shows an apparatus BA containing a gas tight type carbon dioxide detection sensor B according to the present invention. The carbon dioxide detection sensor B is set in a quartz cone 20, and a platinum detection lead 21 and a copper reference lead 22 are connected to opposite faces of the sensor B for detecting the potential. The screw thread 21a allows the contact pressure of the lead 21 to be varied to ensure good electrical contact. As seen in the figure, the top of quartz cone 20 is closed with PTFE lid 23 which allows platinum wire 21 to be connected to a copper lead 24. The PTFE lid 23 also has a test gas inlet tube 25 and outlet tube 26 and the active side of the reference electrode is sealed.

Figure 5:
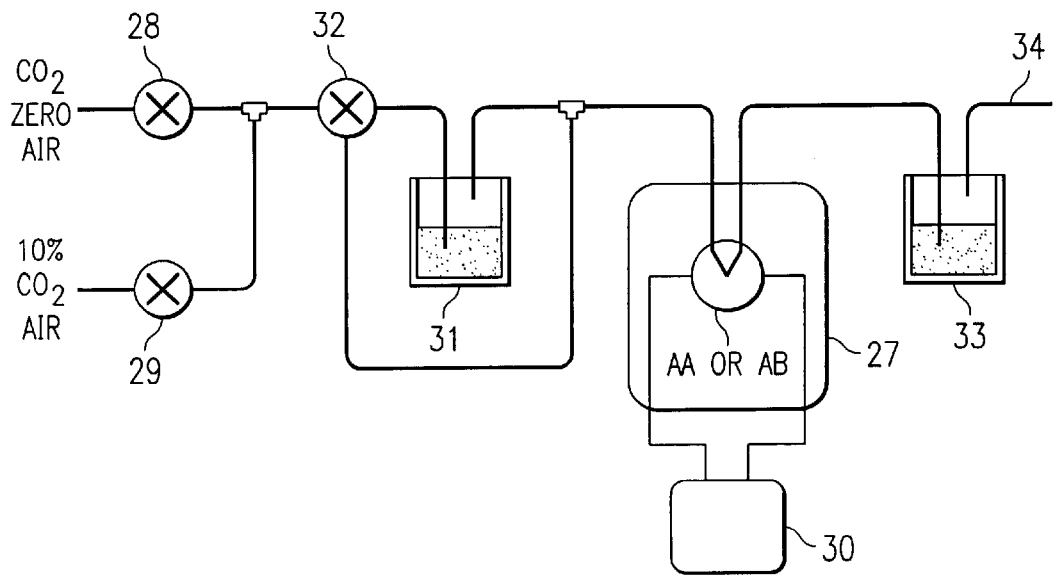
FIG. 5 is a view showing a structure of a device for measuring the cell potential of the sensor relative to gaseous carbon dioxide.

FIG. 5 shows the apparatus AA or BA of the gaseous carbon dioxide detection sensor A or B disposed in a chamber 27 with temperature control. Air with zero carbon dioxide and air with 10% carbon dioxide are mixed through mass flow controllers 28 and 29 respectively to a predetermined concentration and supplied to the chamber 27, and potential differences between the detection electrodes and the reference electrodes 2 and 4 or 7 and 9 are measured by a digital voltmeter 30. In the figure are shown a water vessel 31 for adding a moisture content to the gas to be measured, a flow mixing device 32 to control humidity, a back flow preventive trap 33 and an exhaust opening 34.

Embodiment A uses silver rubidium iodide as the silver ionic conductor 3 and as the ionic conductivity enhancing material for silver carbonate in both detection electrode 2 and reference electrode 4. Thin platinum layers 1 and 5 are formed on both electrodes 2 and 4. Other features are the same as described above.

Figure 6:
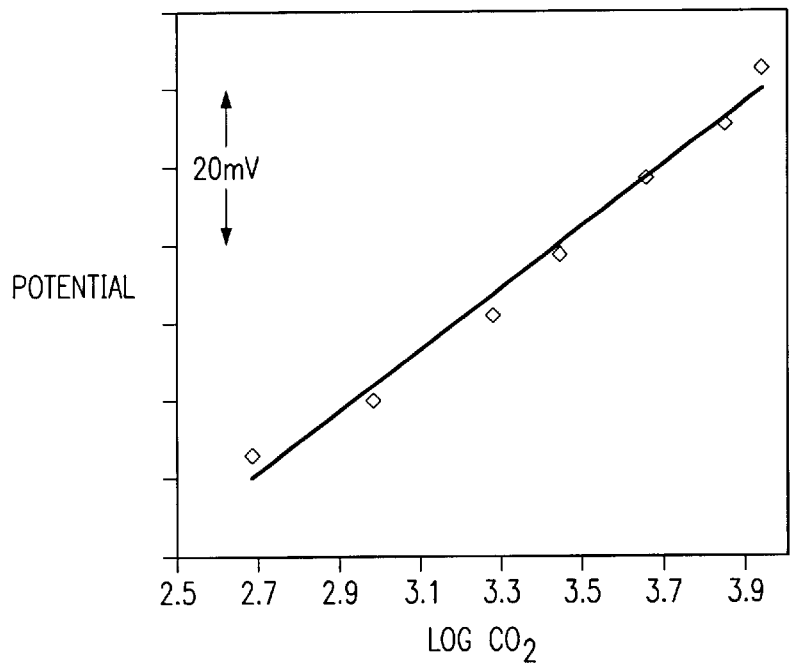
FIG. 6 is a characteristic graph for the cell potential at 25° C. as a function of the log of the carbon dioxide concentration (in ppm) in anhydrous air for an open gas type carbon dioxide detection sensor A.

The gaseous carbon dioxide detection sensor A is demonstrated at low temperatures in the measuring device shown in FIG. 3 and FIG. 5, and the characteristic of the potential difference as a function of gaseous carbon dioxide at concentrations 400 to 9000 ppm was measured in anhydrous air. The results are shown in FIG. 6. As can be seen from the figure, the sensor A shows Nernstian characteristics Embodiment B uses silver rubidium iodide as the silver ionic conductor 8 and as the ionic conductivity enhancing material for silver carbonate in the detection electrode 7 and for part of the reference electrode 9. A thin platinum electrocatalyst layer 6 is formed on the top of detection electrode 7 and a solid silver layer 9 is formed on the reference electrode electrolyte. Other features are the same as described above.

Figure 7:
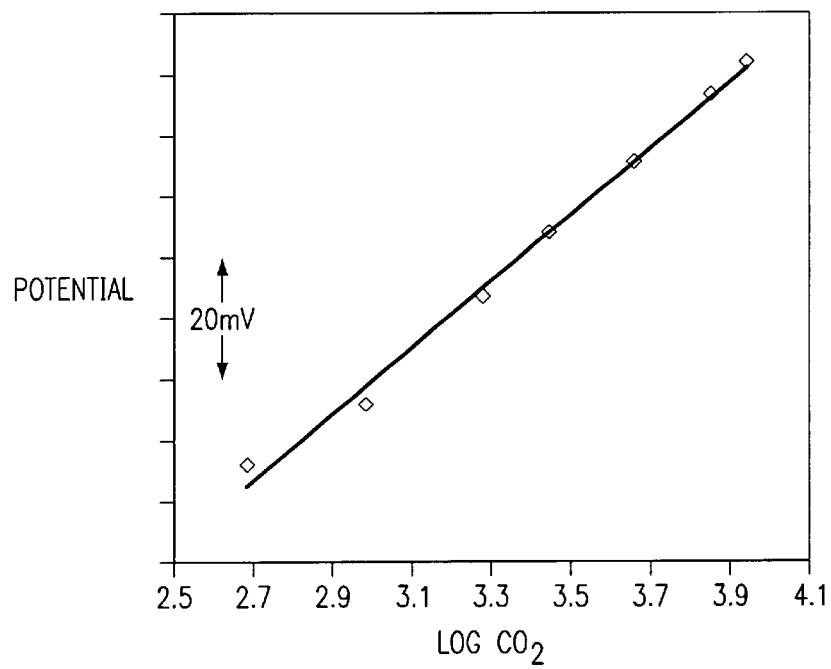
FIG. 7 is a characteristic graph for the cell potential at 25° C. as a function of the log of the carbon dioxide concentration (in ppm) in anhydrous air for a gas tight type carbon dioxide detection sensor B.
Figure 8:
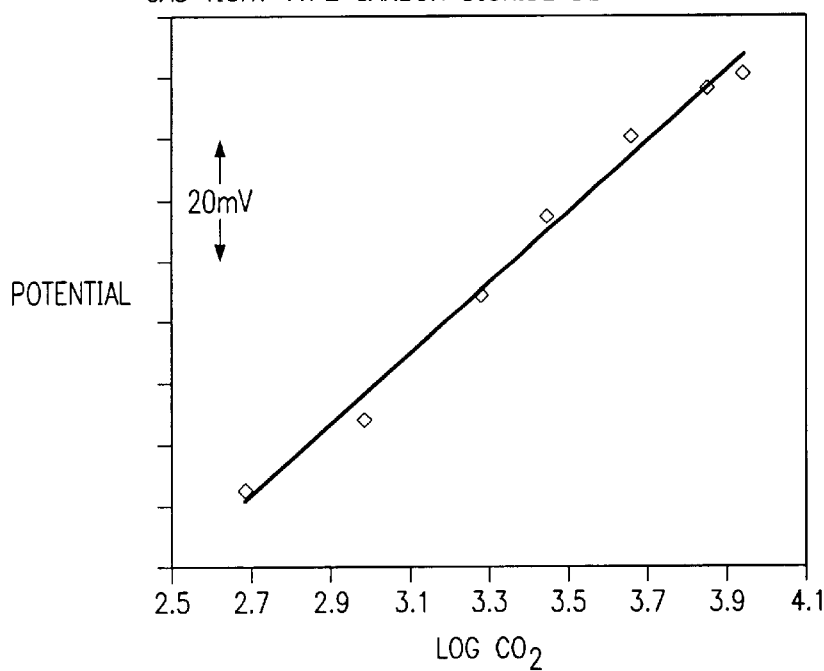
FIG. 8 is a characteristic graph for the cell potential at 25° C. as a function of the log of the carbon dioxide concentration (in ppm) in air with 60% relative humidity for a gas tight type carbon dioxide detection sensor B.

The gaseous carbon dioxide detection sensor B is demonstrated at low temperatures in the measuring device shown in FIG. 4 and FIG. 5, and the characteristic of the potential difference as a function of gaseous carbon dioxide at concentration 400 to 9000 ppm was measured in anhydrous and humid air. The results are shown in FIG. 7 and FIG. 8, respectively. As can be seen from the figures, the sensor B shows linear Nernstian characteristics both in anhydrous air and humid air with 60% relative humidity.

Figure 9:
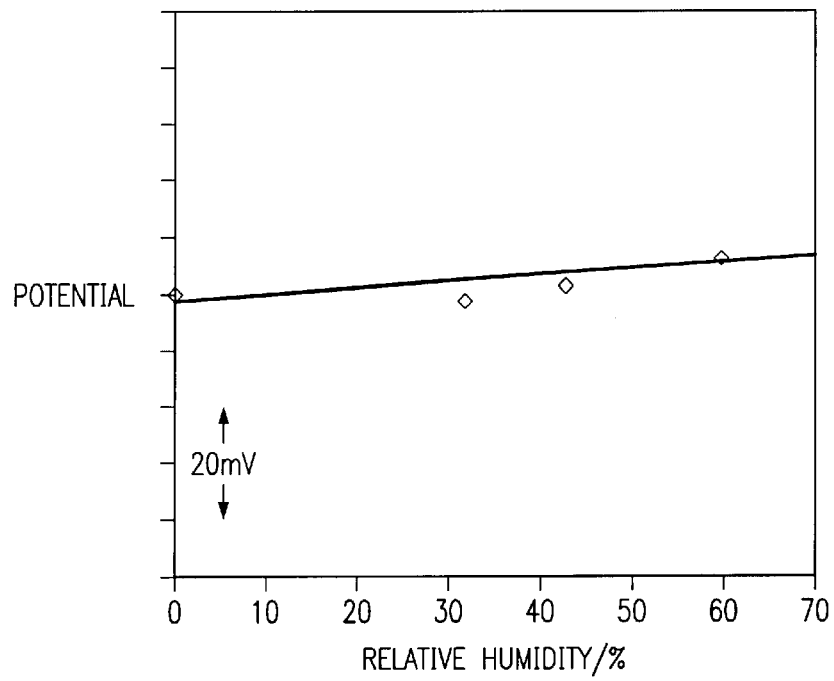
FIG. 9 is a characteristic graph for the cell potential at 25° C. for 8000 ppm of carbon dioxide as a function of the relative humidity for a gas tight type carbon dioxide detection sensor B.

FIG. 9 shows that at 8000 ppm carbon dioxide there is negligible dependence of cell potential on relative humidity in the range 0~60% rh.

Figure 10:
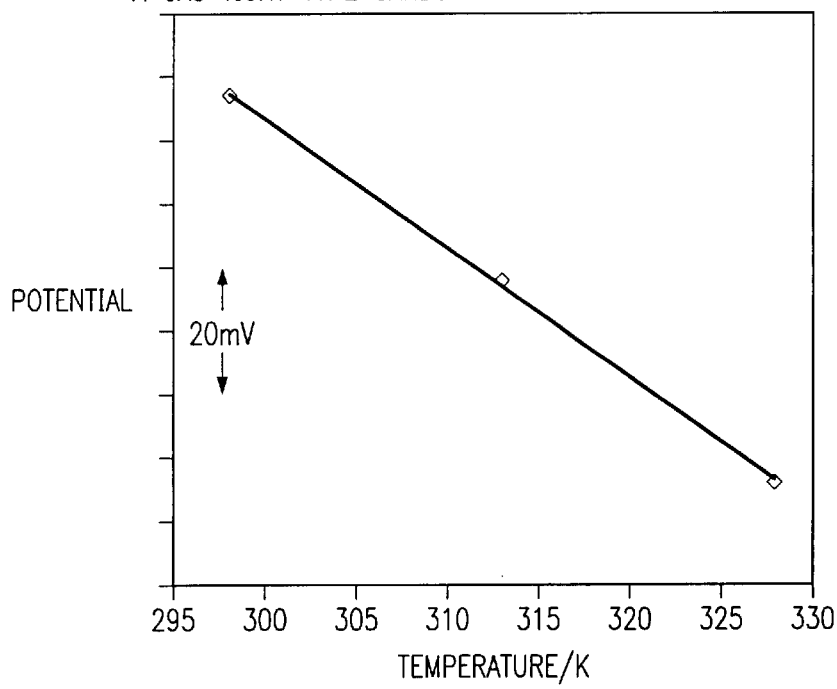
FIG. 10 is a characteristic graph for the cell potential for 2800 ppm of carbon dioxide in anhydrous air as a function of temperature for a gas tight carbon dioxide detection sensor B.

FIG. 10 shows a typical temperature dependence of the cell potential for 2800 ppm of carbon dioxide in anhydrous air. The plot is linear as required by the Nernst Equation.

FIG. 11 and FIG. 12 show typical time responses to step changes in carbon dioxide between 4600 ppm and 8800 ppm in anhydrous air and air with 60% relative humidity, respectively. The 90% response time for both anhydrous and humid air is about 1½ minutes for an increase in carbon dioxide concentration and about 3 minutes for a decrease in carbon dioxide concentration. FIG. 13 shows a typical stability plot for a sensor in 960 ppm of carbon dioxide in anhydrous air at a constant temperature of 25° C. over a period of about 10 days.

We claim:

1. A gas sensor containing an electrolytic cell comprising (A) a detection electrode, (B) a reference electrode, and (C) a solid electrolyte capable of transmitting silver ions, the detection electrode (A) comprising an electrocatalyst, a silver salt the anion of which corresponds to the gas being detected, and a solid electrolyte capable of transmitting silver ions, the reference electrode (B) comprising an electrocatalyst of metallic silver in contact with the solid electrolyte (C), the reference electrode (B) being sealed or in the form of a solid layer.

2. A sensor as claimed in claim 1, wherein the reference electrode is a metallic silver sheet.

3. A sensor as claimed in claim 1, wherein the solid electrolyte in the detection electrode (A) is a silver double salt.

4. A sensor as claimed in claim 3, wherein the detection electrode solid electrolyte is a silver rubidium iodide.

5. A sensor as claimed in claim 1, wherein the electrocatalyst is in the form of a platinum black layer permeable to the gas to be detected.

6. A method of measuring the concentration of a gas in a gas mixture which comprises contacting the gas mixture with the detection electrode of a sensor as claimed in claim 1.

7. A carbon dioxide sensor containing an electrolytic cell comprising (A) a detection electrode, (B) a reference electrode, and (C) a solid electrolyte capable of transmitting silver ions, the detection electrode (A) comprising an electrocatalyst, silver carbonate, and a solid electrolyte capable of transmitting silver ions, the reference electrode (B) comprising an electrocatalyst and a solid electrolyte capable of transmitting silver ions.

8. A sensor as claimed in claim 7, wherein the free face of the reference electrode is in contact with a reference atmosphere.

9. A sensor as claimed in claim 8, wherein the reference atmosphere is air with a known content of carbon dioxide.

10. A sensor as claimed in claim 8, wherein the reference electrode has the same characteristics as the detection 10 electrode.

11. A sensor as claimed in claim 7, wherein the reference electrode is sealed.

12. A sensor as claimed in claim 7, wherein the solid electrolyte in the detection electrode (A) is a silver double salt.

13. A sensor as claimed in claim 12, wherein the detection electrode solid electrolyte is a silver rubidium iodide.

14. A sensor as claimed in claim 7, wherein each electrocatalyst is in the form of a platinum black layer permeable to the gas to be detected.

15. A method of measuring the concentration of carbon dioxide in a gas mixture which comprises contacting the gas mixture with the detection electrode of a sensor as claimed in claim 7.

16. A closed gas type carbon dioxide sensor containing an electrolytic cell comprising a detection electrode, a solid electrolyte, and a reference electrode, the detection electrode comprising an electrocatalyst, silver carbonate, and a silver rubidium iodide, the solid electrolyte comprising a silver rubidium iodide, and the reference electrode comprising a metallic silver sheet in contact with the solid electrolyte.

17. An open gas type carbon dioxide sensor containing an electrolytic cell comprising detection and reference electrodes in contact with a solid electrolyte, the detection and reference electrodes each comprising an electrocatalyst, silver carbonate, and a silver rubidium iodide, and the solid electrolyte comprising a silver rubidium iodide.

* * * * *